United States Patent [19]

Seele et al.

[11] Patent Number: 5,104,438
[45] Date of Patent: Apr. 14, 1992

[54] N-OXOAZOLYLMETHYLOXIRANES AND FUNGICIDES AND BIOREGULATORS CONTAINING THEM

[75] Inventors: Rainer Seele, Fussgoenheim; Eckhard Hickmann, Dannstadt-Schauernheim; Eberhard Ammermann, Ludwigshafen; Gisela Lorenz, Neustadt, all of Fed. Rep. of Germany

[73] Assignee: BASF Aktiengesellschaft, Ludwigshafen, Fed. Rep. of Germany

[21] Appl. No.: 606,950

[22] Filed: Oct. 31, 1990

[30] Foreign Application Priority Data

Nov. 4, 1989 [DE] Fed. Rep. of Germany ....... 3936824

[51] Int. Cl.$^5$ .................. A01N 43/653; C07D 249/08
[52] U.S. Cl. ........................................... 71/92; 71/76; 514/384; 548/267.2; 548/267.8; 548/268.6; 548/268.8
[58] Field of Search ...................... 514/384; 548/268.8, 548/267.2, 247.8, 268.6; 71/92, 76

[56] References Cited

U.S. PATENT DOCUMENTS 4,906,652  3/1990  Karbach et al. .................. 514/383

FOREIGN PATENT DOCUMENTS 094564  11/1983  European Pat. Off. .
196038  10/1986  European Pat. Off. .
315850   5/1989  European Pat. Off. .

*Primary Examiner*—Patricia L. Morris
*Attorney, Agent, or Firm*—Oblon, Spivak, McClelland, Maier & Neustadt

[57] ABSTRACT

N-Oxoazolylmethyloxiranes of the formula I

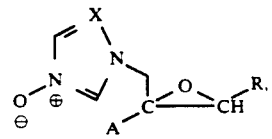

where A and B are identical or different and each is alkyl, cycloalkyl, tetrahydropyranyl, benzyl, norbornyl, naphthyl, biphenyl or phenyl, these radicals being unsubstituted or substituted, and X is CH or N, and fungicides and bioregulators containing them.

10 Claims, No Drawings

N-OXOAZOLYLMETHYLOXIRANES AND FUNGICIDES AND BIOREGULATORS CONTAINING THEM

The present invention relates to novel N-oxoazolylmethyloxiranes of the general formula I

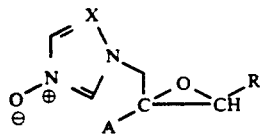

where A and R are identical or different and are each $C_1$-$C_8$-alkyl, $C_3$-$C_8$-cycloalkyl, tetrahydropyranyl, norbornyl, naphthyl, biphenyl or phenyl and these radicals are unsubstituted or monosubstituted to trisubstituted by halogen, nitro, phenoxy, $C_1$-$C_4$-alkyl, $C_1$-$C_4$-alkoxy or $C_1$-$C_4$-haloalkyl, and X is CH or N.

The present invention furthermore relates to a process for the preparation of the compounds I and fungicides containing them.

EP-A 94 564, 196 038 and 315 850 (DEA- 37 37 888) disclose that azolylmethyloxiranes can be used as crop protection agents, in particular fungicides and It is an object of the present invention to provide novel compounds having a similar action spectrum and substantially improved biological activity.

We have found that this object is achieved by the N-oxoazolylmethyloxiranes defined at the outset, which have a better fungicidal action than known azole compounds and are suitable for regulating plant growth.

In formula I, the substituents have the following specific meanings:

A and R independently of one another are each straight-chain or branched $C_1$-$C_8$-alkyl, in particular $C_1$-$C_4$-alkyl, such as methyl, ethyl, propyl, isopropyl, butyl, iso-butyl, sec-butyl or tert-butyl, $C_3$-$C_8$-cycloalkyl, such as cyclopropyl, cyclopentyl or cyclohexyl, tetrahydropyranyl, such as 2-tetrahydropyranyl, 3-tetrahydropyranyl or 4-tetrahydropyranyl, benzyl, phenyl, norbornyl, naphthyl, such as 1-naphthyl or 2-naphthyl, or biphenyl, such as o-, m- or p-biphenyl.

The stated radicals may be monosubstituted to trisubstituted by halogen, such as fluorine, chlorine or bromine, nitro, phenoxy, $C_1$-$C_4$-alkyl, as stated specifically above, $C_1$-$C_4$-alkoxy, e.g. methoxy or ethoxy, or $C_1$-$C_4$-haloalkyl having from 1 to 3 halogen atoms, such as fluorine, chlorine or bromine.

A and R are each preferably phenyl which is unsubstituted or substituted by one, two or three halogen atoms, such as 2-fluorophenyl, 3-fluorophenyl, 4-fluorophenyl, 2-chlorophenyl, 3-chlorophenyl, 4-chlorophenyl, 2-bromophenyl, 3-bromophenyl, 4-bromophenyl, 2,3-difluorophenyl, 2,4-difluorophenyl, 2,5-difluorophenyl, 2,6-difluorophenyl, 3,4-difluorophenyl, 3,5-difluorophenyl, 2,3-difluorophenyl, 2,4-dichlorophenyl, 2,5-dichlorophenyl, 2,6-dichlorophenyl, 3,4-dichlorophenyl, 3,5-dichlorophenyl, 2,3-dibromophenyl, 2,4-dibromophenyl, 2,5-dibromophenyl, 2,6-dibromophenyl, 3,4-dibromophenyl, 3,5-dibromophenyl, 2-chloro-3-fluorophenyl, 3-chloro-2-fluorophenyl, 2-chloro-4-fluorophenyl, 4-chloro-2-fluorophenyl, 2-chloro-5-fluorophenyl, 5-chloro-2-fluorophenyl, 2-chloro-6-fluorophenyl, 3-chloro-4-fluorophenyl, 4-chloro-3-fluorophenyl, 3-chloro-5-fluorophenyl, 2-bromo-3-fluorophenyl, 3-bromo-2-fluorophenyl, 2-bromo-4-fluorophenyl, 4-bromo-2-fluorophenyl, 2-bromo-5-fluorophenyl, 5-bromo-2-fluorophenyl, 2-bromo-6-fluorophenyl, 3-bromo-4-fluorophenyl, 4-bromo-3-fluorophenyl, 3-bromo-5-fluorophenyl, 2-bromo-3-chlorophenyl, 3-bromo-2-chlorophenyl, 2-bromo-4-chlorophenyl, 4-bromo-2-chlorophenyl, 2-bromo-5-fluorophenyl, 5-bromo-2-chlorophenyl, 4-bromo-6-chlorophenyl, 3-bromo-4-chlorophenyl, 4-bromo-3-chlorophenyl or 3-bromo-5-chlorophenyl.

The following radicals are particularly preferred: methyl, ethyl, isopropyl, n-propyl, n-butyl, sec-butyl, tert-butyl, n-pentyl, neopentyl, phenyl, 2-chlorophenyl, 2-fluorophenyl, 2-bromophenyl, 3-chlorophenyl, 3-bromophenyl, 3-fluorophenyl, 4-fluorophenyl, 4-chlorophenyl, 4-bromophenyl, 2,4-dichlorophenyl, 2,3-dichlorophenyl, 2,5-dichlorophenyl, 2,6-dichlorophenyl, 2-chloro-6-fluorophenyl, 2-methoxyphenyl, 3-methoxyphenyl, 4-methoxyphenyl, 2,4-dimethoxyphenyl, 4-ethylphenyl, 4-isopropylphenyl, 4-tert-butylphenyl, 4-tert-butoxyphenyl, 2-chloro-4-fluorophenyl, 2-chloro-6-methylphenyl, 3,4-dimethoxyphenyl, 3-phenoxyphenyl, 4-phenoxyphenyl, 3-nitrophenyl, 4-nitrophenyl, 2-trifluoromethylphenyl, 3-trifluoromethylphenyl or 4-trifluoromethylphenyl.

The compounds of the formula I contain centers of chirality and are generally obtained in the form of racemates or as diastereomer mixtures of erythro or threo forms. In the case of the novel compounds, the erythro or threo diastereomers can be separated in a conventional manner, for example on the basis of their different solubitilities or by column chromatography, and can be isolated in pure form. Pure enantiomers can be obtained by known methods from such a diastereomer which has been isolated. Both the pure diastereomers or enantiomers and mixtures thereof obtained in the synthesis can be used as fungicides.

The N-oxoazolylmethyloxiranes of the formula I can be prepared, for example, by reacting a correspondingly substituted azolylmethyloxirane of the formula II

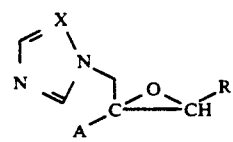

where A, R and X have the meanings stated for the N-oxide I, with a peroxydicarboxylic acid, $H_2O_2$ or an alkyl hydroperoxide and isolating the product in a conventional manner.

Examples of suitable peroxydicarboxylic acids are perbenzoic acid, 3-chloroperbenzoic acid, 4-nitroperbenzoic acid, monoperphthalic acid, peracetic acid, perpropionic acid, monopermaleic acid, monopersuccinic acid, perpelargonic acid and trifluoroperacetic acid.

The peroxycarboxylic acids can also be prepared in situ from the corresponding anhydride and hydrogen peroxide. For example, permaleic acid can be prepared from maleic anhydride and hydrogen peroxide, for example a 30–50% strength by weight aqueous hydrogen peroxide solution. In general, the molar ratios of anhydride to $H_2O_2$ are about 1.5–10, in particular 2–4.

The oxidation with per acids is carried out in aprotic polar solvents, preferably chlorohydrocarbons, e.g.

methylene chloride, chloroform, carbon tetrachloride or dichloroethane, or, if required, in acetic acid, ethyl acetate, acetone or dimethylformamide. In some cases, it may be advantageous to add a conventional buffer, such as sodium acetate, sodium carbonate, disodium hydrogen phosphate or benzyltrimethylammonium hydroxide (Triton ® B), to the reaction mixture.

The reaction temperature is from 10° to 100° C., in particular from 20° to 80° C.

The oxidation can be carried out in the absence of a catalyst or in the presence of a catalyst such as iodine, pyridine N-oxide, sodium tungstate or light.

Other suitable oxidizing agents are alkaline solutions of hydrogen peroxide, for example 30–50% strength by weight aqueous solutions. In this case, suitable solvents are alcohols, such as methanol or ethanol, acetone and acetonitriles. The reaction temperature is, as a rule, lower than when per acids are used as oxidizing agents and is about 10°–50° C., e.g. 25°–30° C.

Furthermore, alkyl hydroperoxides, e.g. tert-butyl hydroperoxide oro cyclohexyl hydroperoxide, can be used as oxidizing agents. In this case, it is advisable to add a catalyst, e.g. sodium tungstate, pertungstic acid, molybdenum hexacarbonyl or vanadyl acetylacetonate. The solvents used can be the abovementioned aprotic polar solvents, for example chlorohydrocarbons.

Preferred oxidizing agents are peroxycarboxylic acids, in particular permaleic acid and m-chloroperbenzoic acid.

The oxidizing agents can be used in amounts of about 1-10, in particular 2-8, moles in the case of peroxycarboxylic acids, about 1-20 moles in the case of hydrogen peroxide and about 1-20 moles in the case of alkyl hydroperoxides, based in each case on 1 mole of starting material II.

The N-oxides I are isolated from the reaction mixture in a conventional manner, for example by subjecting the reaction mixture to chromatographic purification over silica gel.

The starting material II is obtainable by known processes, for example as described in EP-A-94 564, EP-A-196 038 or EP-A-315 850.

The Example which follows illustrates the preparation of the active ingredients.

2-(4-Oxo-1,2,4-triazol-1-ylmethyl)-2-(4-fluorophenyl)-3-(2-chlorophenyl)-oxirane

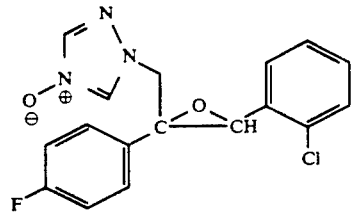

59.4 g (0.60 mole) of maleic anhydride are added to a solutioon of 20 g (0.06 mole) of 2-(1,2,4-triazol-1-ylmethyl)-2-(4-fluorophenyl)-3-(2-chlorophenyl)-oxirane and 0.5 ml of pyridine N-oxide in 150 ml of 1,2-dichloroethane at room temperature. The reaction mixture is cooled to 0° C. and 16.5 g (0.24 mole) of about 50% strength hydrogen peroxide are slowly added. After the end of the addition, the mixture is stirred for two hours at 40°–50° C. and the formation of the N-oxide is monitored by thin-layer chromatography. Thereafter, the precipitated maleic acid is filtered off under suction and the filtrate is washed with sodium bicarbonate solution and water, dried over sodium sulfate and evaporated down under reduced pressure. The subsequent chromatographic purification of the remaining residue over silica gel (4:1 n-hexane/ethyl acetate for isolating the educt; 1:1 ethyl acetate/methanol for isolating the N-oxide) gives 6.3 g (30% of theory) of 2-(4-oxo-1,2,4-triazol-1-yl-methyl)-2-(4-fluorophenyl)-3-(2-chlorophenyl)-oxirane of melting point 216°–218° C.

The compounds shown in the Table can be prepared similarly to Example 1.

TABLE

N-Oxo-azolylmethyloxiranes I

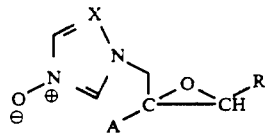

(I)

| Ex. | A | R | X | Physical data m.p./IR |
|---|---|---|---|---|
| 1 | 4-fluorophenyl | 2-chlorophenyl | N | 216–218° C. |
| 2 | 4-fluorophenyl | 2-chlorophenyl | CH | |
| 3 | 4-fluorophenyl | 3-chlorophenyl | N | |
| 4 | 4-fluorophenyl | 3-chlorophenyl | CH | |
| 5 | 4-fluorophenyl | 4-chlorophenyl | N | |
| 6 | 4-fluorophenyl | 4-chlorophenyl | CH | |
| 7 | 4-fluorophenyl | phenyl | CH | |
| 8 | 4-fluorophenyl | phenyl | N | |
| 9 | 4-fluorophenyl | 2,4-dichlorophenyl | N | |
| 10 | 4-fluorophenyl | 2,4-dichlorophenyl | CH | |
| 11 | 4-fluorophenyl | 2-chloro-4-fluorophenyl | N | |
| 12 | 4-fluorophenyl | 2-chloro-4-fluorophenyl | CH | |
| 13 | 4-fluorophenyl | 2-fluorophenyl | N | |
| 14 | 4-fluorophenyl | 2-fluorophenyl | CH | |
| 15 | 4-fluorophenyl | 3-fluorophenyl | N | |
| 16 | 4-fluorophenyl | 3-fluorophenyl | CH | |
| 17 | 4-fluorophenyl | 4-fluorophenyl | N | |
| 18 | 4-fluorophenyl | 4-fluorophenyl | CH | |
| 19 | 4-fluorophenyl | 2,4-difluorophenyl | N | |
| 20 | 4-fluorophenyl | 2,4-difluorophenyl | CH | |
| 21 | 4-fluorophenyl | 2-bromophenyl | N | |

TABLE-continued

N-Oxo-azolylmethyloxiranes I (I)

| Ex. | A | R | X | Physical data m.p./IR |
|---|---|---|---|---|
| 22 | 4-fluorophenyl | 2-bromophenyl | CH | |
| 23 | 4-fluorophenyl | 3-bromophenyl | N | |
| 24 | 4-fluorophenyl | 3-bromophenyl | CH | |
| 25 | 4-fluorophenyl | 4-bromophenyl | N | |
| 26 | 4-fluorophenyl | 4-bromophenyl | CH | |
| 27 | 4-fluorophenyl | 2-methylphenyl | N | |
| 28 | 4-fluorophenyl | 2-methylphenyl | CH | |
| 29 | 4-fluorophenyl | 4-methylphenyl | N | |
| 30 | 4-fluorophenyl | 4-methylphenyl | CH | |
| 31 | 4-fluorophenyl | 2,4-dimethylphenyl | N | |
| 32 | 4-fluorophenyl | 2,4-dimethylphenyl | CH | |
| 33 | 4-fluorophenyl | 4-tert.-butylphenyl | N | |
| 34 | 4-fluorophenyl | 2-methoxyphenyl | N | |
| 35 | 4-fluorophenyl | 2-methoxyphenyl | CH | |
| 36 | 4-fluorophenyl | 4-methoxyphenyl | N | |
| 37 | 4-fluorophenyl | 4-methoxyphenyl | CH | |
| 38 | 4-fluorophenyl | 4-phenoxyphenyl | N | |
| 39 | 4-fluorophenyl | 4-phenoxyphenyl | CH | |
| 40 | 4-fluorophenyl | 4-nitrophenyl | N | |
| 41 | 4-fluorophenyl | 4-nitrophenyl | CH | |
| 42 | 4-fluorophenyl | 2-trifluoromethylphenyl | N | |
| 43 | 4-fluorophenyl | 2-trifluoromethylphenyl | CH | |
| 44 | 4-fluorophenyl | 3-trifluoromethylphenyl | N | |
| 45 | 4-fluorophenyl | 3-trifluoromethylphenyl | CH | |
| 46 | 4-fluorophenyl | 4-trifluoromethylphenyl | N | |
| 47 | 4-fluorophenyl | 4-trifluoromethylphenyl | CH | |
| 48 | 4-fluorophenyl | 1-naphthyl | N | |
| 49 | 4-fluorophenyl | 1-naphthyl | CH | |
| 50 | 4-fluorophenyl | 2-naphthyl | N | |
| 51 | 4-fluorophenyl | 2-naphthyl | CH | |
| 52 | 4-fluorophenyl | 4-biphenyl | N | |
| 53 | 4-fluorophenyl | 4-biphenyl | CH | |
| 54 | 4-fluorophenyl | 4-tetrahydropyranyl | N | |
| 55 | 4-fluorophenyl | 4-tetrahydropyranyl | CH | |
| 56 | 4-fluorophenyl | cyclopropyl | N | |
| 57 | 4-fluorophenyl | cyclopropyl | CH | |
| 58 | 4-fluorophenyl | cyclopentyl | N | |
| 59 | 4-fluorophenyl | cyclopentyl | CH | |
| 60 | 4-fluorophenyl | cyclohexyl | N | |
| 61 | 4-fluorophenyl | cyclohexyl | CH | |
| 62 | 4-fluorophenyl | norbornyl | N | |
| 63 | 4-fluorophenyl | norbornyl | CH | |
| 64 | phenyl | phenyl | N | |
| 65 | phenyl | phenyl | CH | |
| 66 | phenyl | 2-chlorophenyl | N | 194-196° C. |
| 67 | phenyl | 2-chlorophenyl | CH | |
| 68 | phenyl | 3-chlorophenyl | N | |
| 69 | phenyl | 3-chlorophenyl | CH | |
| 70 | phenyl | 4-chlorophenyl | N | |
| 71 | phenyl | 4-chlorophenyl | CH | |
| 72 | phenyl | 2,4-dichlorophenyl | N | |
| 73 | phenyl | 2,4-dichlorophenyl | CH | |
| 74 | phenyl | 2-chloro-4-fluorophenyl | N | |
| 75 | phenyl | 2-chloro-4-fluorophenyl | CH | |
| 76 | phenyl | 2-fluorophenyl | N | |
| 77 | phenyl | 2-fluorophenyl | CH | |
| 78 | phenyl | 3-fluorophenyl | N | |
| 79 | phenyl | 3-fluorophenyl | CH | |
| 80 | phenyl | 4-fluorophenyl | N | |
| 81 | phenyl | 4-fluorophenyl | CH | |
| 82 | phenyl | 2-bromophenyl | N | |
| 83 | phenyl | 2-bromophenyl | CH | |
| 84 | phenyl | 3-bromophenyl | N | |
| 85 | phenyl | 3-bromophenyl | CH | |
| 86 | phenyl | 4-bromophenyl | N | |
| 87 | phenyl | 4-bromophenyl | CH | |
| 88 | phenyl | 2-methylphenyl | N | |
| 89 | phenyl | 2-methylphenyl | CH | |
| 90 | phenyl | 4-methylphenyl | N | |
| 91 | phenyl | 4-methylphenyl | CH | |
| 92 | phenyl | 2,4-dimethylphenyl | N | |
| 93 | phenyl | 2,4-dimethylphenyl | CH | |

TABLE-continued

N-Oxo-azolylmethyloxiranes I (I)

| Ex. | A | R | X | Physical data m.p./IR |
|---|---|---|---|---|
| 94 | phenyl | 2-methoxyphenyl | N | |
| 95 | phenyl | 2-methoxyphenyl | CH | |
| 96 | phenyl | 4-phenoxyphenyl | N | |
| 97 | phenyl | 4-phenoxyphenyl | CH | |
| 98 | phenyl | 2-trifluoromethylphenyl | N | |
| 99 | phenyl | 2-trifluoromethylphenyl | CH | |
| 100 | phenyl | 3-trifluoromethylphenyl | N | |
| 101 | phenyl | 3-trifluoromethylphenyl | CH | |
| 102 | phenyl | 4-trifluoromethylphenyl | N | |
| 103 | phenyl | 4-trifluoromethylphenyl | CH | |
| 104 | phenyl | 1-naphthyl | N | |
| 105 | phenyl | 2-naphthyl | N | |
| 106 | phenyl | cyclohexyl | N | |
| 107 | phenyl | cyclohexyl | CH | |
| 108 | 2-chlorophenyl | phenyl | N | |
| 109 | 2-chlorophenyl | phenyl | CH | |
| 110 | 2-chlorophenyl | 2-chlorophenyl | N | |
| 111 | 2-chlorophenyl | 2-chlorophenyl | CH | |
| 112 | 2-chlorophenyl | 4-chlorophenyl | N | |
| 113 | 2-chlorophenyl | 4-chlorophenyl | CH | |
| 114 | 2-chlorophenyl | 2,4-dichlorophenyl | N | |
| 115 | 2-chlorophenyl | 2,4-dichlorophenyl | CH | |
| 116 | 2-chlorophenyl | 2-fluorophenyl | N | |
| 117 | 2-chlorophenyl | 2-fluorophenyl | CH | |
| 118 | 2-chlorophenyl | 3-fluorophenyl | N | |
| 119 | 2-chlorophenyl | 3-fluorophenyl | CH | |
| 120 | 2-chlorophenyl | 4-fluorophenyl | N | |
| 121 | 2-chlorophenyl | 4-fluorophenyl | CH | |
| 122 | 2-chlorophenyl | 2-trifluoromethylphenyl | N | |
| 123 | 2-chlorophenyl | 2-trifluoromethylphenyl | CH | |
| 124 | 2-chlorophenyl | 3-trifluoromethylphenyl | N | |
| 125 | 2-chlorophenyl | 3-trifluoromethylphenyl | CH | |
| 126 | 2-chlorophenyl | 4-trifluoromethylphenyl | N | |
| 127 | 2-chlorophenyl | 4-trifluoromethylphenyl | CH | |
| 128 | 2-chlorophenyl | 2-methylphenyl | N | |
| 129 | 2-chlorophenyl | 2-methylphenyl | CH | |
| 130 | 2-chlorophenyl | 4-methylphenyl | N | |
| 131 | 2-chlorophenyl | 4-methylphenyl | CH | |
| 132 | 2-chlorophenyl | 4-biphenyl | N | |
| 133 | 2-chlorophenyl | cyclohexyl | N | |
| 134 | 4-chlorophenyl | phenyl | N | |
| 135 | 4-chlorophenyl | phenyl | CH | |
| 136 | 4-chlorophenyl | 2-chlorophenyl | N | 214–215° C. |
| 137 | 4-chlorophenyl | 2-chlorophenyl | CH | |
| 138 | 4-chlorophenyl | 3-chlorophenyl | N | |
| 139 | 4-chlorophenyl | 3-chlorophenyl | CH | |
| 140 | 4-chlorophenyl | 4-chlorophenyl | N | |
| 141 | 4-chlorophenyl | 4-chlorophenyl | CH | |
| 142 | 4-chlorophenyl | 2,4-dichlorophenyl | N | |
| 143 | 4-chlorophenyl | 2,4-dichlorophenyl | CH | |
| 144 | 4-chlorophenyl | 2-fluorophenyl | N | 116° C. |
| 145 | 4-chlorophenyl | 2-fluorophenyl | CH | |
| 146 | 4-chlorophenyl | 3-fluorophenyl | N | |
| 147 | 4-chlorophenyl | 3-fluorophenyl | CH | |
| 148 | 4-chlorophenyl | 4-fluorophenyl | N | |
| 149 | 4-chlorophenyl | 4-fluorophenyl | CH | |
| 150 | 4-chlorophenyl | 2-bromophenyl | N | |
| 151 | 4-chlorophenyl | 2-bromophenyl | CH | |
| 152 | 4-chlorophenyl | 3-bromophenyl | N | |
| 153 | 4-chlorophenyl | 3-bromophenyl | CH | |
| 154 | 4-chlorophenyl | 4-bromophenyl | N | |
| 155 | 4-chlorophenyl | 4-bromophenyl | CH | |
| 156 | 4-chlorophenyl | 2-trifluoromethylphenyl | N | |
| 157 | 4-chlorophenyl | 2-trifluoromethylphenyl | CH | |
| 158 | 4-chlorophenyl | 3-trifluoromethylphenyl | N | |
| 159 | 4-chlorophenyl | 3-trifluoromethylphenyl | CH | |
| 160 | 4-chlorophenyl | 4-trifluoromethylphenyl | N | |
| 161 | 4-chlorophenyl | 4-trifluoromethylphenyl | CH | |
| 162 | 4-chlorophenyl | 2-methylphenyl | N | |
| 163 | 4-chlorophenyl | 2-methylphenyl | CH | |
| 164 | 4-chlorophenyl | 4-methylphenyl | N | |
| 165 | 4-chlorophenyl | 4-methylphenyl | CH | |

TABLE-continued

N-Oxo-azolylmethyloxiranes I (I)

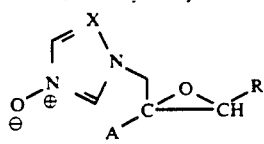

| Ex. | A | R | X | Physical data m.p./IR |
|---|---|---|---|---|
| 166 | 4-chlorophenyl | 1-naphthyl | N | |
| 167 | 4-chlorophenyl | 2-naphthyl | N | |
| 168 | 4-chlorophenyl | 4-tetrahydropyranyl | N | |
| 169 | 4-chlorophenyl | cyclopropyl | N | |
| 170 | 4-chlorophenyl | cyclopropyl | CH | |
| 171 | 4-chlorophenyl | cyclopentyl | N | |
| 172 | 4-chlorophenyl | cyclopentyl | CH | |
| 173 | 4-chlorophenyl | cyclohexyl | N | |
| 174 | 4-chlorophenyl | cyclohexyl | CH | |
| 175 | 2,4-dichlorophenyl | phenyl | N | |
| 176 | 2,4-dichlorophenyl | phenyl | CH | |
| 177 | 2,4-dichlorophenyl | 2-chlorophenyl | N | |
| 178 | 2,4-dichlorophenyl | 2-chlorophenyl | CH | |
| 179 | 2,4-dichlorophenyl | 3-chlorophenyl | N | |
| 180 | 2,4-dichlorophenyl | 3-chlorophenyl | CH | |
| 181 | 2,4-dichlorophenyl | 4-chlorophenyl | N | |
| 182 | 2,4-dichlorophenyl | 4-chlorophenyl | CH | |
| 183 | 2,4-dichlorophenyl | 2,4-dichlorophenyl | N | |
| 184 | 2,4-dichlorophenyl | 2,4-dichlorophenyl | CH | |
| 185 | 2,4-dichlorophenyl | 2-fluorophenyl | N | |
| 186 | 2,4-dichlorophenyl | 2-fluorophenyl | CH | |
| 187 | 2,4-dichlorophenyl | 3-fluorophenyl | N | |
| 188 | 2,4-dichlorophenyl | 3-fluorophenyl | CH | |
| 189 | 2,4-dichlorophenyl | 4-fluorophenyl | N | |
| 190 | 2,4-dichlorophenyl | 4-fluorophenyl | CH | |
| 191 | 2,4-dichlorophenyl | 2-bromophenyl | N | |
| 192 | 2,4-dichlorophenyl | 2-bromophenyl | CH | |
| 193 | 2,4-dichlorophenyl | 2-trifluoromethylphenyl | N | |
| 194 | 2,4-dichlorophenyl | 2-trifluoromethylphenyl | CH | |
| 195 | 2,4-dichlorophenyl | 3-trifluoromethylphenyl | N | |
| 196 | 2,4-dichlorophenyl | 3-trifluoromethylphenyl | CH | |
| 197 | 2,4-dichlorophenyl | 4-trifluoromethylphenyl | N | |
| 198 | 2,4-dichlorophenyl | 4-trifluoromethylphenyl | CH | |
| 199 | 2,4-dichlorophenyl | 2-methylphenyl | N | |
| 200 | 2,4-dichlorophenyl | 2-methylphenyl | CH | |
| 201 | 2,4-dichlorophenyl | cyclohexyl | N | |
| 202 | 2,4-dichlorophenyl | cyclohexyl | CH | |
| 203 | 2-fluorophenyl | phenyl | N | |
| 204 | 2-fluorophenyl | 2-chlorophenyl | N | |
| 205 | 2-fluorophenyl | 4-chlorophenyl | N | |
| 206 | 2-fluorophenyl | 2,4-dichlorophenyl | N | |
| 207 | 2-fluorophenyl | 4-fluorophenyl | N | |
| 208 | 2-fluorophenyl | 4-bromophenyl | N | |
| 209 | 2-fluorophenyl | 2-trifluoromethylphenyl | N | |
| 210 | 2-fluorophenyl | 4-trifluoromethylphenyl | N | |
| 211 | 2-fluorophenyl | 2-methylphenyl | N | |
| 212 | 2-fluorophenyl | cyclopentyl | N | |
| 213 | 4-bromophenyl | phenyl | N | |
| 214 | 4-bromophenyl | phenyl | CH | |
| 215 | 4-bromophenyl | 2-chlorophenyl | N | |
| 216 | 4-bromophenyl | 3-chlorophenyl | N | |
| 217 | 4-bromophenyl | 4-chlorophenyl | N | |
| 218 | 4-bromophenyl | 2,4-dichlorophenyl | N | |
| 219 | 4-bromophenyl | 2-trifluoromethylphenyl | N | |
| 220 | 4-bromophenyl | 4-trifluoromethylphenyl | N | |
| 221 | 4-bromophenyl | 2-methylphenyl | N | |
| 222 | 2-trifluoromethylphenyl | phenyl | N | |
| 223 | 2-trifluoromethylphenyl | 2-chlorophenyl | N | |
| 224 | 2-trifluoromethylphenyl | 4-chlorophenyl | N | |
| 225 | 2-trifluoromethylphenyl | 2,4-dichlorophenyl | N | |
| 226 | 2-trifluoromethylphenyl | 2-trifluoromethylphenyl | N | |
| 227 | 2-trifluoromethylphenyl | 4-trifluoromethylphenyl | N | |
| 228 | 2-trifluoromethylphenyl | 2-fluorophenyl | N | |
| 229 | 2-trifluoromethylphenyl | 4-fluorophenyl | N | |

TABLE-continued

N-Oxo-azolylmethyloxiranes I (I)

| Ex. | A | R | X | Physical data m.p./IR |
|-----|---|---|---|----------------------|
| 230 | 2-trifluoromethylphenyl | 2-methylphenyl | N | |
| 231 | 4-trifluoromethylphenyl | phenyl | N | |
| 232 | 4-trifluoromethylphenyl | phenyl | CH | |
| 233 | 4-trifluoromethylphenyl | 2-chlorophenyl | N | |
| 234 | 4-trifluoromethylphenyl | 4-chlorophenyl | N | |
| 235 | 4-trifluoromethylphenyl | 2-fluorophenyl | N | |
| 236 | 4-trifluoromethylphenyl | 4-fluorophenyl | N | |
| 237 | 4-trifluoromethylphenyl | 2,4-dichlorophenyl | N | |
| 238 | 4-trifluoromethylphenyl | 2-bromophenyl | N | |
| 239 | 4-trifluoromethylphenyl | 2-trifluoromethylphenyl | N | |
| 240 | 4-trifluoromethylphenyl | 4-trifluoromethylphenyl | N | |
| 241 | 4-trifluoromethylphenyl | 2-methylphenyl | N | |
| 242 | 4-trifluoromethylphenyl | 4-methylphenyl | N | |
| 243 | 2-methylphenyl | phenyl | N | |
| 244 | 2-methylphenyl | 2-chlorophenyl | N | |
| 245 | 2-methylphenyl | 4-chlorophenyl | N | |
| 246 | 2-methylphenyl | 2-fluorophenyl | N | |
| 247 | 2-methylphenyl | 4-fluorophenyl | N | |
| 248 | 2-methylphenyl | 4-trifluoromethylphenyl | N | |
| 249 | 4-methylphenyl | phenyl | N | |
| 250 | 4-methylphenyl | 2-chlorophenyl | N | |
| 251 | 4-methylphenyl | 4-chlorophenyl | N | |
| 252 | 4-methylphenyl | 2-fluorophenyl | N | |
| 253 | 4-methylphenyl | 4-fluorophenyl | N | |
| 254 | 4-methylphenyl | 4-trifluoromethylphenyl | N | |
| 255 | 4-tert.-butylphenyl | phenyl | N | |
| 256 | 4-tert.-butylphenyl | 2-chlorophenyl | N | |
| 257 | 4-tert.-butylphenyl | 2-fluorophenyl | N | |
| 258 | 2-methoxyphenyl | phenyl | N | |
| 259 | 2-methoxyphenyl | 2-chlorophenyl | N | |
| 260 | 2-methoxyphenyl | 4-chlorophenyl | N | |
| 261 | 2-methoxyphenyl | 2-fluorophenyl | N | |
| 262 | 2-methoxyphenyl | 4-fluorophenyl | N | |
| 263 | 4-methoxyphenyl | phenyl | N | |
| 264 | 4-methoxyphenyl | 2-chlorophenyl | N | |
| 265 | 4-methoxyphenyl | 4-chlorophenyl | N | |
| 266 | 4-methoxyphenyl | 2-fluorophenyl | N | |
| 267 | 4-methoxyphenyl | 4-fluorophenyl | N | |
| 268 | 4-methoxyphenyl | 2,4-dichlorophenyl | N | |
| 269 | 4-biphenyl | phenyl | N | |
| 270 | 4-biphenyl | 2-chlorophenyl | N | |
| 271 | 4-biphenyl | 4-chlorophenyl | N | |
| 272 | 4-biphenyl | 2-fluorophenyl | N | |
| 273 | 4-biphenyl | 4-fluorophenyl | N | |
| 274 | 4-phenoxyphenyl | phenyl | N | |
| 275 | 4-phenoxyphenyl | 2-chlorophenyl | N | |
| 276 | 4-phenoxyphenyl | 4-chlorophenyl | N | |
| 277 | 4-phenoxyphenyl | 4-fluorophenyl | N | |
| 278 | 1-naphthyl | 2-chlorophenyl | N | |
| 279 | 1-naphthyl | 4-chlorophenyl | N | |
| 280 | 1-naphthyl | 4-fluorophenyl | N | |
| 281 | 2-naphthyl | 4-phenoxyphenyl | N | |
| 282 | 2-naphthyl | 2-chlorophenyl | N | |
| 283 | 2-naphthyl | 4-chlorophenyl | N | |
| 284 | 2-naphthyl | 4-fluorophenyl | N | |
| 285 | 4-tetrahydro- | 2-chlorophenyl | N | |

TABLE-continued
N-Oxo-azolylmethyloxiranes I

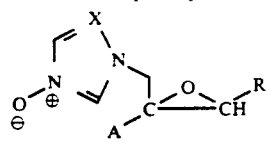

(I)

| Ex. | A | R | X | Physical data m.p./IR |
|---|---|---|---|---|
| 286 | 4-tetrahydro-pyranyl | 4-chlorophenyl | N | |
| 287 | 4-tetrahydro-pyranyl | 2-fluorophenyl | N | |
| 288 | 4-tetrahydro-pyranyl | 4-fluorophenyl | N | |
| 289 | 4-tetrahydro-pyranyl | 2,4-dichlorophenyl | N | |
| 290 | methyl | phenyl | N | |
| 291 | methyl | 2-chlorophenyl | N | |
| 292 | methyl | 4-chlorophenyl | N | |
| 293 | methyl | 2,4-dichlorophenyl | N | |
| 294 | methyl | 2-fluorophenyl | N | |
| 295 | methyl | 4-fluorophenyl | N | |
| 296 | methyl | 2-bromophenyl | N | |
| 297 | methyl | 4-trifluoromethylphenyl | N | |
| 298 | methyl | 2-trifluoromethylphenyl | N | |
| 299 | tert.-butyl | phenyl | N | |
| 300 | tert.-butyl | phenyl | CH | |
| 301 | tert.-butyl | 2-chlorophenyl | N | |
| 302 | tert.-butyl | 2-chlorophenyl | CH | |
| 303 | tert.-butyl | 4-chlorophenyl | N | |
| 304 | tert.-butyl | 4-chlorophenyl | CH | |
| 305 | tert.-butyl | 2,4-dichlorophenyl | N | |
| 306 | tert.-butyl | 2,4-dichlorophenyl | CH | |
| 307 | tert.-butyl | 4-fluorophenyl | N | |
| 308 | tert.-butyl | 4-fluorophenyl | CH | |
| 309 | tert.-butyl | 2-fluorophenyl | N | |
| 310 | tert.-butyl | 2-fluorophenyl | CH | |
| 311 | tert.-butyl | 4-trifluoromethylphenyl | N | |
| 312 | tert.-butyl | 4-trifluoromethylphenyl | CH | |
| 313 | tert.-butyl | 2-bromophenyl | N | |
| 314 | tert.-butyl | 2-bromophenyl | CH | |
| 315 | tert.-butyl | 2-methylphenyl | N | |
| 316 | tert.-butyl | 2-methylphenyl | CH | |
| 317 | tert.-butyl | 1-naphthyl | N | |
| 318 | tert.-butyl | 2-naphthyl | N | |
| 319 | tert.-butyl | cyclohexyl | N | |
| 320 | tert.-butyl | cyclohexyl | CH | |
| 321 | cyclohexyl | phenyl | N | |
| 322 | cyclohexyl | phenyl | CH | |
| 323 | cyclohexyl | 2-chlorophenyl | N | |
| 324 | cyclohexyl | 2-chlorophenyl | CH | |
| 325 | cyclohexyl | 4-chlorophenyl | N | |
| 326 | cyclohexyl | 4-chlorophenyl | CH | |
| 327 | cyclohexyl | 2,4-dichlorophenyl | N | |
| 328 | cyclohexyl | 2,4-dichlorophenyl | CH | |
| 329 | cyclohexyl | 2-fluorophenyl | N | |
| 330 | cyclohexyl | 2-fluorophenyl | CH | |
| 331 | cyclohexyl | 4-fluorophenyl | N | |
| 332 | cyclohexyl | 4-fluorophenyl | CH | |
| 333 | cyclohexyl | 2-trifluoromethylphenyl | N | |
| 334 | cyclohexyl | 2-trifluoromethylphenyl | CH | |
| 335 | cyclohexyl | 4-trifluoromethylphenyl | N | |
| 336 | cyclohexyl | 4-trifluoromethylphenyl | CH | |
| 337 | cyclohexyl | 2-bromophenyl | N | |
| 338 | cyclohexyl | 2-bromophenyl | CH | |
| 339 | cyclohexyl | 2-methylphenyl | N | |
| 340 | cyclohexyl | 2-methylphenyl | CH | |
| 341 | cyclohexyl | 4-biphenyl | N | |
| 342 | cyclohexyl | 2-naphthyl | N | |
| 343 | cyclohexyl | 2-methoxyphenyl | N | |
| 344 | cyclohexyl | cyclohexyl | N | |

In general terms, the novel compounds are extremely effective on a broad spectrum of phytopathogenic fungi, in particular those from the class consisting of the Ascomycetes and Basidiomycetes. Some of them have a systemic action and can be used as foliar and soil fungicides.

The fungicidal compounds are of particular interest for controlling a large number of fungi in various crops or their seeds, especially wheat, rye, barley, oats, rice, Indian corn, lawns, cotton, soybeans, coffee, sugar cane, fruit and ornamentals in horticulture and viticulture, and in vegetables such as cubumbers, beans and cucurbits.

The novel compounds are particularly useful for controlling the following plant diseases:

*Erysiphe graminis* in cereals,
*Erysiphe cichoracearum* and *Sphaerotheca fuliginea* in cucurbits,
*Podosphaera leucotricha* in apples,
*Uncinula necator* in vines,
Puccinia species in cereals,
*Rhizoctonia solani* in cotton,
Ustilago species in cereals and sugar cane,
*Venturia inaequalis* (scab) in apples,
Helminthosporium species in cereals,
*Septoria nodorum* in wheat,
*Botrytis cinerea* (gray mold) in strawberries and grapes,
*Cercospora arachidicola* in groundnuts,
*Pseudocercosporella herpotrichoides* in wheat and barley,
*Pyricularia oryzae* in rice,
*Phytophthora infestans* in potatoes and tomatoes,
*Fusarium and Verticillium* species in various plants,
*Plasmopara viticola* in grapes,
*Alternaria species* in fruit and vegetables.

The compounds are applied by spraying or dusting the plants with the active ingredients, or treating the seeds of the plants with the active ingredients. They may be applied before or after infection of the plants or seeds by the fungi.

The novel substances can be converted into conventional formulations such as solutions, emulsions, suspensions, dusts, powders, pastes and granules. The application forms depend entirely on the purposes for which they are intended; they should at all events ensure a fine and uniform distribution of the active ingredient. The formulations are produced in known manner, for example by extending the active ingredient with solvents and/or carriers, with or without the use of emulsifiers and dispersants; if water is used as solvent, it is also possible to employ other organic solvents as auxiliary solvents. Suitable auxiliaries for this purpose are solvents such as aromatics (e.g., xylene), chlorinated aromatics (e.g., chlorobenzenes), paraffins (e.g., crude oil fractions), alcohols (e.g., methanol, butanol), ketones (e.g., cyclohexanone), amines (e.g., ethanolamine, dimethylformamide), and water; carriers such as ground natural minerals (e.g., kaolins, aluminas, talc and chalk) and ground synthetic minerals (e.g., highly disperse silica and silicates); emulsifiers such as nonionic and anionic emulsifiers (e.g., polyoxyethylene fatty alcohol ethers, alkyl sulfonates and aryl sulfonates); and dispersants such as lignin, sulfite waste liquors and methylcellulose.

The fungicides generally contain from 0.1 to 95, and preferably from 0.5 to 90, wt % of active ingredient. The application rates are from 0.02 to 3 kg or more of active ingredient per hectare, depending on the type of effect desired. The novel compounds may also be used for protecting materials (timber), .e.g., against *Paecilomyces variotii*.

The agents and the ready-to-use formulations prepared from them, such as solutions, emulsions, suspensions, powders, dusts, pastes and granules, are applied in conventional manner, for example by spraying, atomizing, dusting, scattering, dressing or watering.

Examples of formulations are given below.

I. A solution of 90 parts by weight of compound no. 1 and 10 parts by weight of N-methyl-α-pyrrolidone, which is suitable for application in the form of very fine drops.

II. A mixture of 20 parts by weight of compound no. 1, 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzenesulfonic acid, and 5 parts by weight of the adduct of 40 moles of ethylene oxide and 1 mole of castor oil. By finely dispersing the mixture in water, an aqueous dispersion is obtained.

III. An aqueous dispersion of 20 parts by weight of compound no. 1, 40 parts by weight of cyclohexanone, 30 parts by weight of isobutanol, 20 parts by weight of the adduct of 40 moles of ethylene oxide and 1 mole of castor oil. By pouring the mixture into water and finely distributing it therein, an aqueous dispersion is obtained.

IV. An aqueous dispersion of 20 parts by weight of compound no. 1, 25 parts by weight of cyclohexanol, 65 parts by weight of a mineral oil fraction having a boiling point between 210° and 280° C., and 10 parts by weight of the adduct of 40 moles of ethylene oxide and 1 mole of castor oil. By pouring the mixture into water and finely distributing it therein, an aqueous dispersion is obtained.

V. A hammer-milled mixture of 80 parts by weight of compound no. 1, 3 parts by weight of the sodium salt of diisobutylnaphthalene-α-sulfonic acid, 10 parts by weight of the sodium salt of a lignin-sulfonic acid obtained from a sulfite waste liquor, and 7 parts by weight of powdered silica gel. By finely dispersing the mixture in water, a spray liquor is obtained.

VI. An intimate mixture of 3 parts by weight of compound no. 1 and 97 parts by weight of particulate kaolin. The dust contains 3 wt % of the active ingredient.

VII. An intimate mixture of 30 parts by weight of compound no. 1, 92 parts by weight of powdered silica gel and 8 parts by weight of paraffin oil sprayed onto the surface of this silica gel. This formulation of the active ingredient exhibits good adherence.

VIII. A stable aqueous dispersion of 40 parts by weight of compound no. 1, 10 parts of the sodium salt of a phenolsulfonic acid-urea-formaldehyde condensate, 2 parts of silica gel and 48 parts of water, which dispersion can be further diluted.

IX. A stable oily dispersion of 20 parts by weight of compound no. 1, 2 parts by weight of the calcium salt of dodecylbenzenesulfonic acid, 8 parts by weight of a fatty alcohol polyglycol ether, 2 parts by weight of the sodium salt of a phenolsulfonic acid-urea-formaldehyde condensate and 68 parts by weight of a paraffinic mineral oil.

The N-oxoazolylmethyloxiranes of the formula I may exercise a variety of influences on practically all plant development stages, and are therefore used as growth regulators. The diversity of action of bioregulators depends especially on a) the type and variety of plant;
b) the time applied, with reference to the development stage of the plants and the time of the year;
c) the place and method of application (seed treatment, soil treatment, or application to foliage);
d) climatic factors, e.g., average temperature, amount of precipitate, sunshine and duration;
e) soil conditions (including fertilization);
f) the formulation of the active ingredient; and g) the concentration at which the active ingredient is applied.

A description of some of the various possibilities of using the bioregulators according to the invention in agriculture and horticulture is given below.

A. Vegetative plant growth can be inhibited to a considerable extent, a fact which is manifested particularly in a reduction in plant height. The treated plants thus have a compact habit; furthermore, the leaf color is darker.

Of advantage in practice is for example the reduction in grass growth on roadsides, hedges, canal embankments and on areas such as parks, sportsgrounds, fruit orchards, lawns and airfields, thus reducing expensive and time-consuming mowing.

A further feature of economic interest is the increase in the rigor of crops which tend to lodge, such as cereals, Indian corn, sunflowers and soybeans. The shortening and strengthening of the stem thus caused reduces or eliminates the danger of lodging under unfavorable weather conditions.

The use of growth regulators is also important for inhibiting plant height and changing the time of ripening in cotton. It is thus possible for this important crop to be harvested completely mechanically.

The use of compounds I may also increase or inhibit lateral branching. This is of interest when, for instance in tobacco plants, it is desired to inhibit the formation of lateral shoots (suckers) in favor of leaf development.

With the compounds I, it is possible for instance in winter rape to considerably increase the resistance to freeze injury. On the one hand, upward growth and the development of a too luxuriant (and thus particularly frost-susceptible) leaf or plant mass are inhibited; on the other, the young rape plants are kept, in spite of favorable growth conditions, in the vegetative development stage before winter frosts begin. The danger of freeze injury is thus eliminated in plants which tend to lose prematurely their inhibition to bloom and pass into the generative phase. In other crops, too, e.g., winter cereals, it is advantageous if the plants are well tillered in the fall as a result of treatment with the compounds according to the invention, but enter winter with not too lush a growth. This is a preventive measure against increased susceptibility to freeze injury and—because of the relatively low leaf or plant mass—attack by various (especially fungus) diseases. The inhibition of vegetative growth also makes closer planting possible in numerous crops, which means an increase in yield, based on the area cropped.

B. Better yields both of plant parts and plant materials may be obtained with agents based on N-oxoazolylmethyloxiranes I. It is thus for instance possible to induce increased formation of buds, blossom, leaves, fruit, seed grains, roots and tubers, to increase the sugar content of sugarbeets, sugarcane and citrus fruit, to raise the protein content of cereals and soybeans, and to stimulate the increased formation of latex in rubber trees.

The N-oxoazolylmethyloxiranes of the formula I may rise the yield by influencing plant metabolism or by promoting or inhibiting vegetative and/or generative plant growth.

C. It is also possible with the N-oxoazolylmethyloxiranes of the formula I to shorten or lengthen growth stages and to accelerate or retard the ripening process in plant parts either before or after harvesting.

A factor of economic interest is for example the facilitation of harvesting made possible by a chemical, temporally concentrated loosening (abscission) of the adherence of stalks to the branches of citrus fruit, olive trees, and other kinds of pomes, drupes and indehiscent fruit. The same mechanism, i.e., promotion of the formation of separation layers between fruit or leaf and stem of the plant, is also essential for a readily controllable defoliation of crop plants, e.g., cotton.

D. Further, transpiration in crop plants may be reduced with growth regulators. This is particularly important for plants growing in agricultural areas which are expensive to irrigate, e.g., in arid or semi-arid areas. Irrigation frequency can be reduced by using the compounds according to the invention, making for lower costs. As a result of the use of growth regulators, the water available can be better utilized, because, inter alia,
the size of the stomata opening is reduced;
a thicker epidermis and cuticle are formed;
penetration of the soil by the roots is improved;
the micro-climate in the stand is favorably influenced by the more compact growth.

The active ingredients according to the invention may be applied not only to the seed (as a dressing), but also to the soil, i.e., via the roots, and to the foliage by spraying.

As a result of the good tolerance of the compounds I by crop plants, the application rate may vary within wide limits. When seed is treated, active ingredient amounts of from 0.001 to 50, and preferably from 0.01 to 1, g per kg of seed are generally required. When the soil or the foliage is treated, amounts of from 0.01 to 10, and preferably from 0.1 to 5, kg/ha are generally sufficient.

Formulations generally contain from 0.1 95, and preferably from 0.5 to 90, wt % of active ingredient.

In these application forms, the agents based on azolylmethyloxiranes of the formula I may also be present together with other active ingredients, for example herbicides, insecticides, growth regulators, and fungicides, and may furthermore be mixed and applied together with fertilizers. Admixture with other fungicides may result in synergistic effects, i.e., the action of the combination product is greater than the added actions of the individual components.

We claim:

1. A compound of the formula I

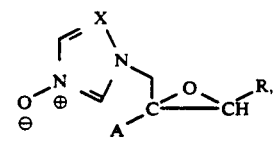

where A and R are identical or different and each is selected from the group consisting of $C_1$-$C_8$-alkyl, $C_3$-$C_8$-cycloalkyl, tetrahydropyranyl, benzyl, norbornyl, naphthyl, biphenylyl or phenyl, these radicals being unsubstituted or mono- to trisubstituted by halogen, nitro, phenoxy, $C_1$-$C_4$-alkyl, $C_1$-$C_4$-alkoxy or $C_1$-$C_4$-haloalkyl, and X is N.

2. A fungicidal composition comprising an inert carrier and a fungicidally effective amount of a compound of claim 1.

3. A process for combating fungi, wherein a fungicidally effective amount of a compound of claim 1, is applied to the fungi or the plant materials, plant areas, plants or seed threatened by fungus attack.

4. A compound of claim 1, wherein A is 4-fluorophenyl and R is 2-chlorophenyl.

5. A compound of claim 1, wherein A is phenyl and R is 2-chlorophenyl.

6. A compound of claim 1, wherein A is 4-chlorophenyl and R is 2-chlorophenyl.

7. A compound of claim 1, wherein A is 4-chlorophenyl and R is 2-fluorophenyl.

8. A compound according to claim 1, wherein A and R independently are unsubstituted phenyl, fluoro-substituted phenyl, or chloro-substituted phenyl.

9. A composition for regulating plant growth comprising an inert carrier and an amount of a compound of claim 1, effective for regulating plant growth.

10. A process for regulating plant growth wherein the soil, the seed and/or the plants are treated with an amount effective to regulate plant growth of a compound according to claim 1.

* * * * *